(12) United States Patent
Brockway et al.

(10) Patent No.: US 8,321,036 B2
(45) Date of Patent: Nov. 27, 2012

(54) CARDIAC RHYTHM MANAGEMENT DEVICE

(75) Inventors: Brian Brockway, Shoreview, MN (US); Marina V. Brockway, Shoreview, MN (US)

(73) Assignee: Data Sciences International, Inc., St. Paul, MN (US)

( * ) Notice: Subject to any disclaimer, the term of this patent is extended or adjusted under 35 U.S.C. 154(b) by 47 days.

(21) Appl. No.: 13/087,997

(22) Filed: Apr. 15, 2011

(65) Prior Publication Data

US 2011/0190835 A1 Aug. 4, 2011

Related U.S. Application Data

(63) Continuation of application No. 12/163,720, filed on Jun. 27, 2008, now abandoned, which is a continuation-in-part of application No. 11/223,587, filed on Sep. 8, 2005, now abandoned, which is a continuation-in-part of application No. 10/799,931, filed on Mar. 12, 2004, now abandoned, application No. 13/087,997, which is a continuation-in-part of application No. 11/728,190, filed on Mar. 22, 2007, now abandoned, which is a continuation-in-part of application No. 10/077,566, filed on Feb. 15, 2002, now abandoned.

(51) Int. Cl.
*A61N 1/362* (2006.01)
(52) U.S. Cl. .......................................... 607/129; 607/23
(58) Field of Classification Search .................... 607/23, 607/129
See application file for complete search history.

(56) References Cited

U.S. PATENT DOCUMENTS

| | | | |
|---|---|---|---|
| 4,846,191 A | 7/1989 | Brockway et al. |
| 4,967,749 A | 11/1990 | Cohen |
| 5,083,563 A | 1/1992 | Collins |
| 5,184,614 A | 2/1993 | Collins et al. |
| 5,282,840 A | 2/1994 | Hudrlik |
| 5,454,377 A | 10/1995 | Dzwonczyk et al. |
| 5,814,089 A | 9/1998 | Stokes et al. |
| 6,033,366 A | 3/2000 | Brockway et al. |
| 6,141,588 A | 10/2000 | Cox et al. |
| 6,296,615 B1 | 10/2001 | Brockway et al. |
| 6,666,826 B2 | 12/2003 | Salo et al. |
| 6,882,882 B2 | 4/2005 | Struble et al. |
| 6,915,157 B2 | 7/2005 | Bennett et al. |
| 7,236,819 B2 | 6/2007 | Brockway et al. |
| 7,369,901 B1 | 5/2008 | Morgan et al. |
| 2002/0120200 A1 | 8/2002 | Brockway et al. |
| 2003/0191402 A1 | 10/2003 | Arzbaecher et al. |
| 2004/0172081 A1 | 9/2004 | Wang |
| 2005/0065445 A1 | 3/2005 | Arzbaecher et al. |

OTHER PUBLICATIONS

Braunwald et al., Studies on Starling's law of the heart. III. Observations in patients with mitral stenosis and atrial fibrillation on the relationships between left ventricular end-diastolic segment length, filling pressure, and the characteristics of ventricular contraction, *J. Clin. Invest.*, 1960, 39(12): 1874-1884.

(Continued)

*Primary Examiner* — Brian T Gedeon
(74) *Attorney, Agent, or Firm* — Fish & Richardson P.C.

(57) ABSTRACT

A medical device is disclosed for implantation on an epicardial surface of the heart. The device has a transmural member providing optimal electrode locations for various therapies. The hemodynamically optimal therapy is guided by sensed left ventricular pressure and electrical activity. The device may be used alone or with a companion implanted cardiac rhythm management device.

22 Claims, 6 Drawing Sheets

OTHER PUBLICATIONS

Byrd et al. "Comparison of conventional and biventricular antitachycardia pacing in a geometrically realistic model of the rabbit ventricle," *Journal of Cardiovacsular Electrophysiology*, 2004, 15(9): 1066-1077.

DiCori et a l, "New-onset ventricular tachycardia after cardiac resynchronization therapy," *J. Interv. Card. Electrophysiol.*, 2005, 23: 231-235.

Guerra et al., "Increase in ventricular tachycardia frequency after biventricular implantable cardioverter defibrillator upgrade," *J. Cardiovasc. Electrophysiol.*, 2003, 14: 1245-1247.

Muntinga et al., Left ventricular diastolic function after electrical cardioversion of atrial fibrillation,: *Heart*, 2002, 87(4): 379-380.

Pak et al., Synchronization of ventricular fibrillation with real-time feedback pacing: implication to low-energy defibrillation, *Am J. Physiol. Heart Circ. Physiol.*, 2003, 285: H2704-H2711.

Turitto, "Cardiac Resynchronization therapy: A review of proarrhythmic and antiarrhythmic mechanisms," *Pacing and Clinical Electrophysiology*, 2007, 30(1): 115-122.

Turrito et al, "Torsade de pointes: An electrophysiological effect of cardiac resynchronization?" *Pacing Clin. Electrophysiol.*, 2006, 29: 520-522.

van Gelder et al., "The hemodynamic effect of intrinsic conduction during left ventricular pacing as compared to biventricular pacing," *J. Am. Coll. Cardiol.*, 2005, 46(12): 2305-2310.

CARDIAC RHYTHM MANAGEMENT DEVICE

CROSS REFERENCE TO RELATED APPLICATIONS

The present case claims the benefit of and (a) is a continuation of U.S. patent application Ser. No. 12/163,720, now abandoned, filed Jun. 27, 2008, and entitled "Cardiac Rhythm Management Device," which is a continuation-in-part of U.S. patent application Ser. No. 11/223,587, now abandoned, filed Sep. 8, 2005, and entitled "Implantable Pressure Sensor with Pacing Capability," and which is also a continuation-in-part of U.S. patent application Ser. No. 10/799,931, now abandoned, filed Mar. 12, 2004, and entitled "Pressure Transmission Catheters for Implantable Pressure Sensors," and (b) is a continuation-in-part of U.S. patent application Ser. No. 11/728,190, now abandoned, filed Mar. 22, 2007, and entitled "Devices, Systems and Methods for Endocardial Pressure Measurement," which is a continuation of U.S. patent application Ser. No. 10/077,566, now abandoned, filed Feb. 15, 2002, and entitled "Devices, Systems and Methods for Endocardial Pressure Measurement." Each of the above-mentioned parent applications are incorporated by reference herein in their entirety.

FIELD OF THE INVENTION

The present invention relates to systems and implantable medical devices for managing cardiac rhythms of a heart, and in particular a class of systems that include an implantable medical device that is attached to an external surface of a heart chamber, for example, a left ventricle.

BACKGROUND

Cardiac pacing for rhythm abnormalities began in the 1960s with demand pacing. In these devices a sensed ventricular depolarization (VS) started an escape interval timer. In the absence of another ventricular sense event during the escape interval, the pacer device would time out and deliver a ventricular pacing stimulus (VP) to the right ventricle (RV) of the heart. This modality (VVI) provides a rate floor for the patient. Normal sinus rhythm (NSR) above this rate floor will be sensed and used to reset the escape interval timer to "inhibit" the pacemaker output stimulus.

These devices are successfully used to treat patients with a too slow heart rate (bradycardia). To further improve the cardiac output the atrio-ventricular, or AV sequential pacemaker, was introduced. The AV sequential pacemaker (DVI) will likely stimulate the atrium (AP) prior to stimulating the ventricle (VP). This improves the cardiac output due to increased filling of the ventricles as described by "Starlings Law". The time interval between the atrial pace (AP) or atrial sense (AS) events and the ventricular stimulus (VP) in this dual chamber modality (DVI) is called the AV delay, and the AV delay is typically a physician programmable parameter, although some devices employ algorithms that perform a form of adaptive AV delay. Further refinement of dual chamber pacing has resulted in devices which sense and pace in both chambers of the right heart. Dual demand (DDD/DDI) pacers can manage heart rhythm over a wide range of conduction disorders.

In the 1980s automatic implantable defibrillators (AID) entered use to deliver defibrillation shock to interrupt bouts of ventricular fibrillation (VF) or ventricular tachycardia (VT) in patients exhibiting sudden death syndrome. These AID devices detected ventricular electrogram (EGM) information from an indwelling lead system and delivered a high voltage current to the heart. Advances in this therapy have included the adoption of transvenous lead systems and the incorporation of tiered therapy.

A tiered ICD device can pace or cardiovert or defibrillate as required. Such devices can deliver stimuli that extend from low energy pacing therapy through cardioversion and anti-tachycardia therapies such as burst stimulation and ramped stimulation of ventricular chambers. The stimulation train hierarchy attempts to convert an arrhythmia before a need arises to administer defibrillation shocks.

For patients with a fast but regular heart rhythm (ventricular tachycardia, VT), various protocols for administering anti-tachycardia pacing therapy (ATP) have been proposed and implemented as part of a tiered therapy device.

One strategy widely used calls for fast pacing at a rate near the observed tachycardia rate. The delivery of ventricle burst stimuli will interrupt a reentry circuit or entrain the rhythm. For patients where ventricular tachyarrhythmia accelerates to ventricular fibrillation (VF), the implanted cardiovertor defibrillators must quickly default to a high energy defibrillation regime. The defibrillation shock delivers a relatively large amount of energy to the heart to depolarize critical mass of myocardium at once. With luck a normal sinus rhythm develops after the global refractory period of the tissues. The electrical field distribution is such that nearby skeletal muscles are stimulated as well. This results in very painful therapy that is typically invoked when a high ventricular rate is observed for several seconds. Sometimes the patient experiences an electric pause and needs bradycardia pacing support after the shock.

It has been discovered more recently that patients with heart failure (HF) benefit from cardiac resynchronization therapy (CRT) where two synchronized ventricular stimuli are provided. In such a case that employs multiple leads, multiple output circuits, one for each lead, may be used. One VP stimulus is provided to the right ventricle (RV), and the other stimulus is provided to the left ventricle (LV). It has been also demonstrated by Berry M. van Gelder et. al. in "The Hemodynamic Effect of Intrinsic Conduction During Left Ventricular Pacing as Compared to Biventricular Pacing," *J. Am. Coll. Cardiol.* 2005; 46; 2305-2310, that left ventricular pacing is hemodynamically superior to biventricular pacing in CRT when fusion with intrinsic conduction over the right bundle is present. If both chambers are stimulated, the delay between the stimulation of the two chambers VtoV (VV) is selected to mimic the progression of a normal ventricular depolarization wavefront around the heart.

SUMMARY

In general, this document describes systems that employ various embodiments of an implantable device that includes a housing and a transmural member that extends from the housing. The implantable device may be implanted such that the device housing rests against an epicardial surface of a ventricular wall (for example, a left ventricular wall) and the transmural member extends entirely through the ventricular wall so that its distal end is positioned within a ventricular chamber. In various configurations, the systems may perform various pacing, cardioverting, and defibrillation therapies.

There are three primary embodiments of the invention but there are many variations in implementation. For example, there are several electrode configurations proposed. In many instances the optimal electrode placement is dictated by patient cardiovascular disease, for example, bradycardia or tachycardia or heart failure. For this reason among others the devices are shown with electrodes that may be optional or not required for some patients and for some therapies. Other optional features such as one or more pressure transducers may or may not be present in an embodiment. A pressure transducer signal may be used alone or in combination with electrical signals to detect a change and invoke a therapy.

A reading from a companion pressure transducer may be used to compensate a reading from an intracardiac pressure transducer to direct therapy or it may be used to collect diagnostic information to be relayed to a remote diagnostic receiver. For these reasons the embodiments shown should be seen as illustrative and non-limiting as substantial variations are contemplated within the scope of the claims.

Each embodiment of the invention includes a small implantable device housing that is placed on the outside epicardial surface of the left ventricle of the patient's heart. The device housing is anchored on the epicardial surface. A transmural member that carries electrodes is provided in each embodiment. The transmural member may have any number of electrodes but three rings are shown for clarity and to facilitate explanation of the invention.

In many embodiments, but not all embodiments the transmural member carries a pressure transducer. In some implementations the member is hollow and is filled with a gel or fluid that communicates LV pressure to a sensor residing in the device housing. However other sensor locations along the transmural member are contemplated. For example and as an alternative, a pressure sensor may be incorporated into the member body itself at a location remote from the device housing. In the figures several pressure sensor locations are proposed, and multiple uses for the pressure data are given. It should be understood that other variations are contemplated within the scope of the invention. In some instances the pressure sensor incorporated into the transmural member may be positioned within the LV chamber or within the myocardium in a manner that permits the measurement of LV pressure on a beat to beat basis by the device.

The electronic components within the device perform many functions as is common in this art. These electronic components may compensate pressures measured from the LV space for variations in atmospheric pressure or compensation may take place external to the body. Once compensated, the information is used for several purposes.

In most embodiments a primary cell is provided within the device housing. However in other embodiments the device housing receives power from a companion device. In the remotely powered embodiments a charging circuit is used to charge up a storage element such as a capacitor or recharge a secondary cell within the housing and the stored charge is used to power the device.

In a first "Pacemaker" embodiment the epicardial device housing is placed on the wall of the left ventricle and pacing stimuli are delivered at that location in accordance with conventional pacing protocols. Superior electrode involvement with the left ventricle is expected to provide for optimal conduction patterns. Pressure data if available can be used to optimize AV delay times thus providing hemodynamically optimal pacing. A combination of pressure and EGM signals can be used in the detection and discrimination of far field atrial events to support atrial tracking pacing modes.

Disclosed with this and subsequent embodiments is a secondary companion pressure sensor located on or within the device housing to monitor intrathoracic pressure. The data can be used in several ways. For example, the secondary companion pressure sensor may be used to measure intrathoracic pressure, and from those measurements determine a respiration rate of the patient, which may be used, for example, for rate responsive pacing therapies. In such a case, the secondary pressure sensor may be the only pressure sensor employed in the system (and in that sense, not a companion sensor), or the secondary sensor may indeed be used in combination with one or more other pressure sensors, for example, a pressure sensor that senses left ventricular pressure. As another example of how the data from the secondary companion pressure sensor may be used, such data may be used to correct for atmospheric or ambient pressure changes the left ventricular pressure measurements that are taken, for example, by another pressure sensor associated with a catheter that extends into the left ventricle.

Disclosed with this embodiment is an electrode array that places several discrete electrode sites near the location of the device. This array of companion electrodes has many uses and may be shared with the other embodiments.

In a second "Defibrillation" embodiment, the device may be coupled to one or more defibrillation electrodes that may be positioned, for example, on the right ventricle (RV). In this embodiment the implanted device can provide a limited number of defibrillation shocks if required with favorable energy and current distribution to minimize skeletal muscle stimulation. The device can provide conventional pacing therapy as well as conventional biventricular therapies. Pressure data if available can be used to optimize VT, VF detection and discrimination.

In a third "Transducing Lead" embodiment the device may be connected to a conventional ICD though an LV lead port on the ICD. Alternatively the epicardial device may be connected to a companion device that supplies power and may also provide other functions such as telemetry of information to and from the epicardial device. In this configuration the device functions in part as a passive LV lead but it also can send LV pressure data to the ICD to optimize therapy or detect a need for defibrillation. In this embodiment the device may command the ICD. In this embodiment the ICD can also power the epicardial device.

Summarizing and in some instances restating the above, in one aspect an implantable device is provided for managing heart rhythm. The device includes a device housing for implantation on the epicardial surface of the left ventricular wall. The device also includes a transmural member extending from said device housing and adapted for implantation across the left ventricular wall. Further yet, the device includes one or more electrodes located on said transmural member, said electrodes to perform one or more of the following functions: a) sensing or b) pacing. The device also includes logic located within said device housing for pacing the left ventricle in response to electrical activity of the heart.

In various implementations, such an implantable device may include one or more of the following features. The device may further includes a pressure sensor proximate the device housing for measuring left ventricular pressure. In such a case, the logic located within the device housing may pace the left ventricle in response to electrical activity of the heart and measured left ventricular pressure. An array of electrodes may be attached to the device housing and located on the epicardial surface of the left ventricular wall. The logic of the device may carry out bradycardia and antitachy cardiac pacing modalities. In such a case, for bradycardia modalities that call for an AV delay interval, the AV delay is determined at least in part from said measured left ventricular pressure and sensed electrical activity of the heart.

In addition or alternatively, such an implantable device may further include a reference pressure transducer associated with said device housing for monitoring intrathoracic pressure. In such a case, the reference pressure transducer may be used to detect respiration. In addition in such a case, the device may be adapted to adjust pacing based on metabolic demand determined from detected respiration. The reference pressure transducer may additionally or alternatively be used compensate the LV pressure measurements.

Further yet for such an implantable device, the transmural member may include multiple different electrodes formed on a surface of the transmural member. The transmural member may include both electrically conductive portions and non-electrically conductive portions.

In a second aspect, there is provided an implantable device for managing heart rhythm that includes the following components: a device housing for implantation on the epicardial surface of the left ventricular wall; a transmural member extending from said device housing said transmural member adapted for implantation in the left ventricular wall; one or more electrodes located on said transmural member, said electrodes to perform one or more of the following functions: a) sensing or b) pacing; a right ventricular lead connectable to said device housing; and logic located within said device housing for pacing the left ventricle and/or the right ventricle in response to electrical activity of the heart.

In such an implantable device of this second aspect that includes the additional right ventricular lead, the device may further include a pressure sensor proximate said device housing for measuring left ventricular pressure. In such a case, the logic located within said device housing may pace the left ventricle and the right ventricle in response to electrical activity of the heart and the measured left ventricular pressure. In such a case, the logic may additionally or alternatively carry out bradycardia antitachy pacing modalities. In addition, the AV delay and/or the RV to LV pacing intervals may be determined by the measured left ventricular pressure and electrogram.

In a third aspect, a system is provided that includes an implantable epicardial device for managing a heart rhythm in combination with a subcutaneous device of the type having a lead connector. In such a case, the implantable epicardial device includes a device housing for implantation on the epicardial surface of the left ventricular wall; a coupling lead connecting said subcutaneous device with said device housing, for coupling said subcutaneous device and said epicardial device together; a transmural member extending from said epicardial device housing said transmural member adapted for implantation in the left ventricular wall; one or more electrodes located on said transmural member, said electrodes to perform one or more of the following functions: a) sensing or b) pacing; a pressure transducer proximate said epicardial device housing for measuring left ventricular pressure and providing pressure data to said subcutaneous device; and logic for measuring LV pressure data and transmitting the data to said subcutaneous device to invoke a defibrillation therapy based at least in part on sensed ventricular pressures.

In such a system of the third aspect, the coupling lead may transfer power to the epicardial device housing. In such a case, the coupling lead may transfer pacing energy to the epicardial device housing for delivery to the one or more electrodes. The coupling lead may transfer defibrillation energy to the epicardial device housing for delivery to the one or more electrodes. In addition, the failure to convert an arrhythmia may result in the telemetry of a warning signal to a remote receiver. The implantable device of the system may be connected to a pacemaker, and alternatively or additionally, to an ICD.

In a fourth aspect, there is provided an implantable cardiac rhythm management system. The system includes an assembly comprising a housing and an elongate structure that extends from the housing and includes thereon one or more electrodes. The assembly is adapted to be delivered and secured to an epicardial surface of a ventricular wall such that upon being secured to the ventricular wall the assembly housing remains external of the heart while the assembly elongate structure extends through (or into) the ventricular wall. The system also includes a lead connectable to the assembly (for example, at a proximal end of the lead) and includes a flexible lead body that extends from the assembly and includes one or more electrodes (for example, at a distal end of the lead). The lead is of a length such that when the assembly is secured to a left ventricular wall and the lead is connected to the assembly, the one or more electrodes of the lead are positionable adjacent to a right ventricular wall. In the housing of the assembly there is contained circuitry for analyzing cardiac electrical activity sensed by the electrodes of the system and for issuing stimulation pulses that are delivered between two or more of the electrodes of the system.

BRIEF DESCRIPTION OF THE DRAWINGS

Throughout the figures of the drawing identical reference numerals indicate identical structure wherein.

DETAILED DESCRIPTION

Overview

The several embodiments of the invention are presented in sequence and the functionality shared among various embodiments may be described only once in the specification although the functionality may be used or incorporated into other later described embodiments.

Bradycardia Pacing

Many of the embodiments of the invention carry out pacing modalities to treat a too slow rhythm. Dual chamber, single chamber and atrial tracking modalities such as DDD; DDI; DVI; VVI; and others are well known and detailed explanations are not necessary to carry them out in the implanted device. In general many parameters are set by the physician via remote telemetry to tailor the device to the needs of the patient. One such parameter may be a hemodynamically optimal AV delay interval.

A companion intrathoracic pressure sensor can be used to measure respiration parameters and adjust pacing scheme based on metabolic demand, and can also serve to obtain a surrogate of barometric pressure to correct measurements from the LV pressure sensor for changes in barometric pressure.

Antitachy Pacing

Pacing therapies that deliver low level electrical stimulation to the ventricles to interrupt VT are well known.

Examples of these therapies are burst stimulation and ramped stimulation, to name a few. In general these modalities are used to interrupt the arrhythmia and they are preferred to high voltage defibrillation therapies when they are effective. The distributed electrode configurations described below will increase surface area with minimal increase in current demand thus permit more effective ATP pacing independent of the stimulation waveform or synchrony.

Cardiac Resynchronization Therapy

Bi-ventricular stimulation of ventricles in sequence or left ventricular stimulation alone have been shown to improve cardiac function especially in patients with congestive heart failure. Dual stimulation of the RV and LV is known and the relative timing of the two stimuli is selected to better mimic the natural depolarization wave as it progresses around the heart. In general this VtoV timing interval is a physician selected parameter. At present, a primary indication for CRT is heart failure with cardiac output not meeting metabolic demand. Optimization of pacing parameters, including AV delay is aimed to increase cardiac output. The pressure parameters are used in the example embodiments described below as a validated surrogate of cardiac output. This optimization should improve the ejection fraction for all pacing modalities described.

Detailed Descriptions of Illustrative Embodiments

Pacemaker Embodiment

Figure 1:
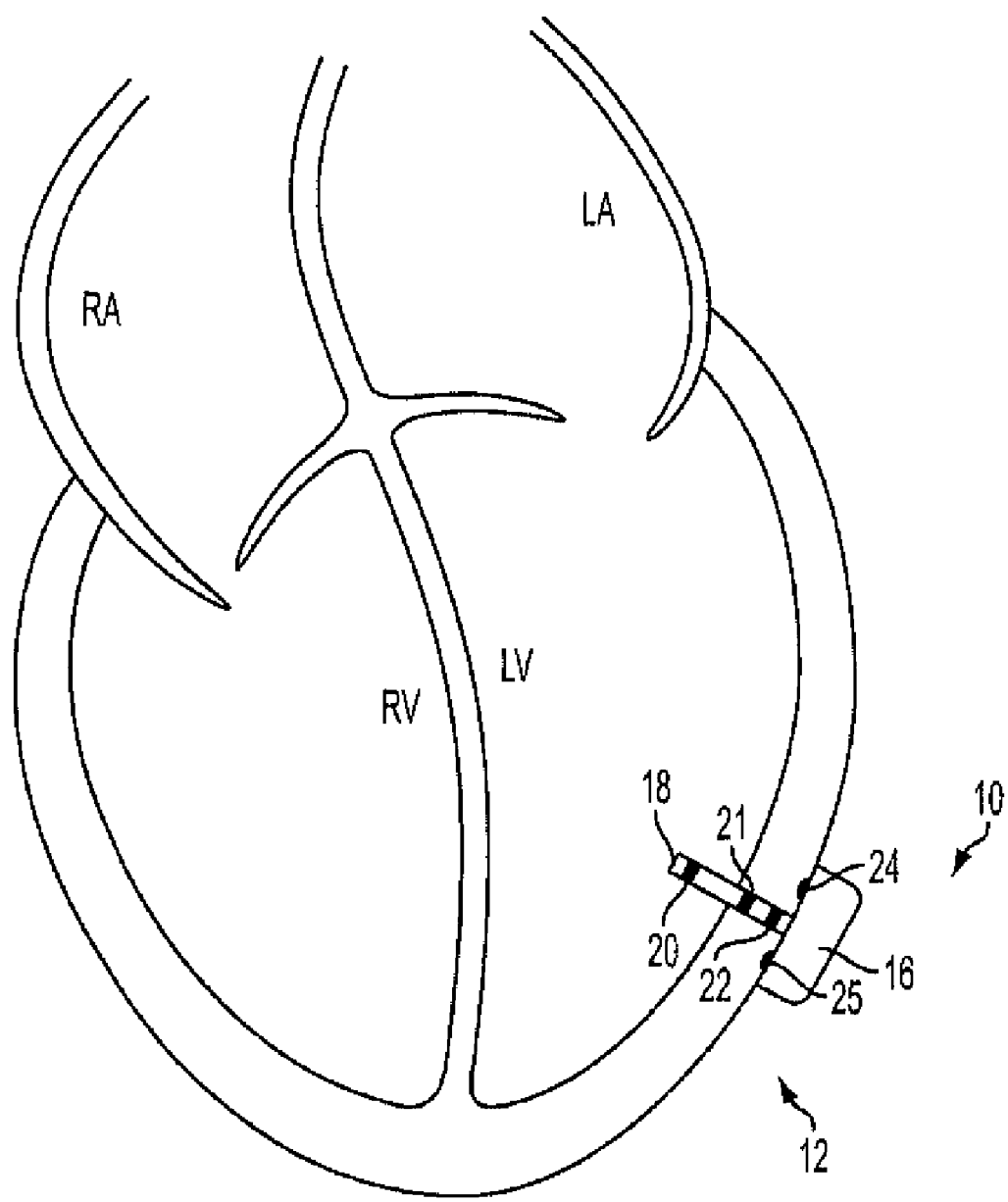
FIG. 1 is a schematic presentation of the first embodiment of the invention.
Figure 2:
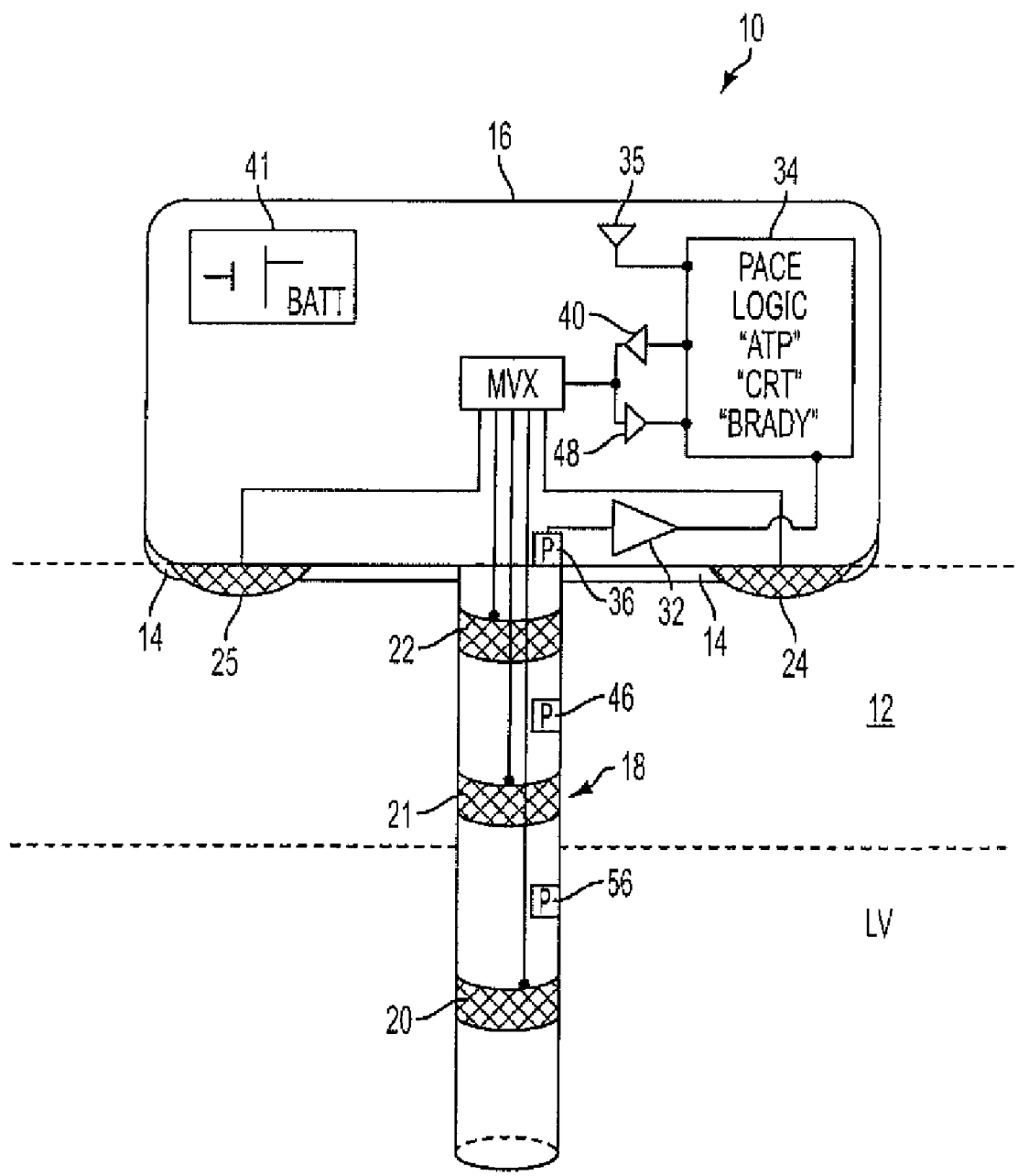
FIG. 2 is a schematic presentation of the first embodiment of the invention.

FIGS. 1 and 2 show an implantable device 10 attached to the epicardial wall of the left ventricle (LV) 12. There are a number of fixation strategies that may be employed including the use of tines, clips or adhesives. One illustrative fixation device is a polyester fabric (such as Dacron) or other fabric that promotes fibrous tissue in-growth. In such a device, a fabric fixation patch 14 is attached to a surface of the device housing 16 that is positioned against the LV wall 12 to permit and promote tissue in-growth to anchor the device 10 to the wall 12.

A transmural member 18 extends from the device housing 16 and across the LV wall 12. In one implementation, the transmural member 18 is a pressure transmission catheter. In such an implementation, the pressure transmission catheter has a lumen formed therein that extends the length of the catheter. The lumen is filled with a pressure transmission fluid, such that pressure forces acting upon a distal end of the pressure transmission catheter are transmitted through the fluid in the catheter to a proximal end of the pressure transmission catheter, and acts upon a pressure transducer, such as pressure transducer 36. In another implementation, the transmural member 18 is not used to sense pressure within a heart chamber, and may be, for example, a solid elongate structure.

It is advantageous for the transmural member 18 to have a length and electrode positioning that achieves electrical stimulation at an endocardial location of the tissue. There is variability in thickness of ventricular walls from patient to patient. For example, some patients may have a ventricular wall as thin as about eight millimeters, while other patients may have a ventricular wall as thick as about 20 millimeters. The length of transmural member 18 may be provided in various sizes so as to accommodate the wall thickness.

In the embodiment shown in FIGS. 1-2, three separate ring electrodes are positioned on the transmural member 18 to both stimulate the myocardium and to sense the myocardial EGM at that location. The ring electrodes are labeled 20, 21 and 22 in the figure. More or fewer electrodes may be placed on this member 18. In the exemplary configuration, a distal-most ring electrode 20 is located on the member 18 such that it becomes positioned in the blood pool of the LV, while a middle ring electrode 21 is located on the member 18 so that it becomes positioned in the illustrated implantation within the LV wall 12, between the epicardium and endocardium. A proximal-most ring electrode 22 is located on the member 18 near the device housing 16, such that it also becomes positioned in the illustrated implantation within the LV wall 12.

Each of the three ring electrodes 20, 21 and 22 in the FIG. 1-2 embodiment is connected to a separate lead wire that extends proximally through the member 18 and into the housing 16. As such, it is possible, in this embodiment, to provide electrical stimulation between any two of the electrodes 20, 21 and 22 on the member 18, for example, between the distal-most electrode 20 and the middle electrode 21. There being multiple electrodes on the transmural member 18 provides the benefit of stimulation pulses that are more targeted into endocardial tissue regions, and thus more effective.

In addition, the fact that the transmural member 18 is not entirely made of a conductive material (that is, entirely a single stimulation electrode) may have further advantages that may be important. For example, the portion of the member 18 that is not covered by electrically conductive material (portions between each of the electrodes 20, 21 and 22, and portions distal of electrode 20 and proximal of electrode 22) may be made of a material that aids in tissue in-growth. The material may be, for example, a porous material of a specific pore size into which tissue grows. The transmural member 18 configuration described in this document may therefore enable the reduction of any complications that may result from a device being positioned through a ventricular wall.

In addition to the electrodes on the device tranmural member 18, the device housing 16 itself may be used as an electrode, and two epicardial electrodes are shown as well. The epicardial electrodes are labeled 24 and 25 in the figure. The epicardial electrodes 24 and 25 are located on the same surface of the housing 16 from which the transmural member 18 extends, that is, for the surface of the housing 16 that is positioned against the LV wall 12. In addition, the electrodes 24 and 25 may extend through the fabric attached to the housing 16 discussed above.

The implantable device 10 has electronic components to carry out bradyarrhythmia pacing protocols that call for pacing the ventricle. In addition, atrial tracking pacing protocols can be achieved, as well by far field sensing of atrial events from the electrodes seen in the figure. Detailed description of the pacing protocols and methods to implement them are not required as they are well known in this field. However far field sensing requires some discussion.

Modern pacemaker or ICDs are set up to filter atrial events from a bipolar ventricular EGM. In the normal context such sensing is regarded as an artifact that can still sometimes be observed on ventricular EGM signal. In such a device, atrial lead sensing electrodes are used to detect atrial events and set the timing intervals associated with atrial tracking pacing modes. The proposed device, by contrast, may in some embodiments employ remote sensing (that is, sensing from a ventricular location where the device 10 is positioned) of atrial events to support some pacing protocols. Different filter settings and signal processing techniques will enable atrial event detection.

As alluded to previously, the use in an epicardial device of electrodes deep within the LV wall or in the LV space near the LV wall—as opposed to epicardial electrodes that are on the epicardial surface of the LV wall or only extend a small distance into the LV wall 12—allows for transmural and or endocardial pacing that ensures more natural impulse propagation and better synchrony between LV and RV contraction.

In embodiments where pressure data is available from a pressure sensor associated with the transmural catheter 18 further detection criteria can be established to discriminate the atrial signals.

FIG. 2 shows in more detail the implantable device 10 in isolation while components in the housing 16 are illustrated schematically. The transmural catheter 18 is coupled to a pressure sensor 36 that transduces the LV pressure to a signal conditioned by interface circuit 38. The transduced signal provides pressure data to the logic circuit 34.

The logic circuit 34 carries out many functions and may issue a ventricular pace (VP) command or VP signal to activate a stimulation circuit 40. A stimulus when required may be delivered to one or more of the ring electrodes (for example, electrode 20, 21 or 22) that is referenced to another nearby electrode (for example, electrode 20, 21, 22, 24, 25, or an electrode associated with the device housing 16). Other pacing and sensing electrode configurations are possible with the optional companion electrodes.

When a pressure transducer is used such as a transducer at one of locations 36 or 46 or 56, a pressure time history of a heartbeat is available for analysis. It will be understood that although multiple pressure transducers are shown in FIG. 2, only one such transducer may be sufficient, and that the multiple different transducers being shown in the figure is for purposes of showing different locations in which the transducer may be implemented. As discussed previously, pressure transducer 36 may be in communication with a pressure transmission medium contained in a lumen within the transmural member 18. The same may be true for pressure transducers 46 and 56. See, for example, U.S. Pat. Nos. 4,846,191; 6,033,366; and 6,296,615, all assigned to the assignee of the present patent application. In alternative implementations, different types of pressure sensors may be employed.

The pressure trace or recording obtained may show inflection points corresponding to valve motion and contraction and relaxation. The EGM signals from electrodes processed by sense amplifier 48 represent both near field ventricular electrical activity as well as far field sensing of atrial events. A combination of frequency domain and time domain signal processing in the logic 34 extracts the atrial and ventricular events from the combined EGM and LV pressure signals.

The LV pressure and EGM history may also permits the measurement of actual A to V activation times, as well as selecting or determining a pacing AV delay to maximize cardiac output. This process may be updated frequently and potentially on a beat to beat basis. Telemetry circuitry associated with logic 34 and radio frequency transmitter 35 can be used by an external programmer to set pacing parameters for the device 10 in any known atrial or ventricular synchronized pacing mode. The AV delay of the pacing mode can be adjusted manually or automatically to a hemodynamically optimal value. Diagnostic data may also be made available to the physician via the telemetry system.

A companion intrathoracic pressure sensor located on device housing (not shown in FIGS. 1-2, but shown in the FIG. 4 embodiment, as pressure sensor 57, and will be described in more detail later) can be used to measure respiration parameters and adjust AV interval and pacing rate based on metabolic demand.

In addition to the above-noted features and components, the device 10 shown in FIGS. 1 and 2 may also include an array of epicardial surface ATP electrodes that will be described in connection with FIGS. 3A, 3B and 4.

Defibrillation Embodiment

Figure 3A:
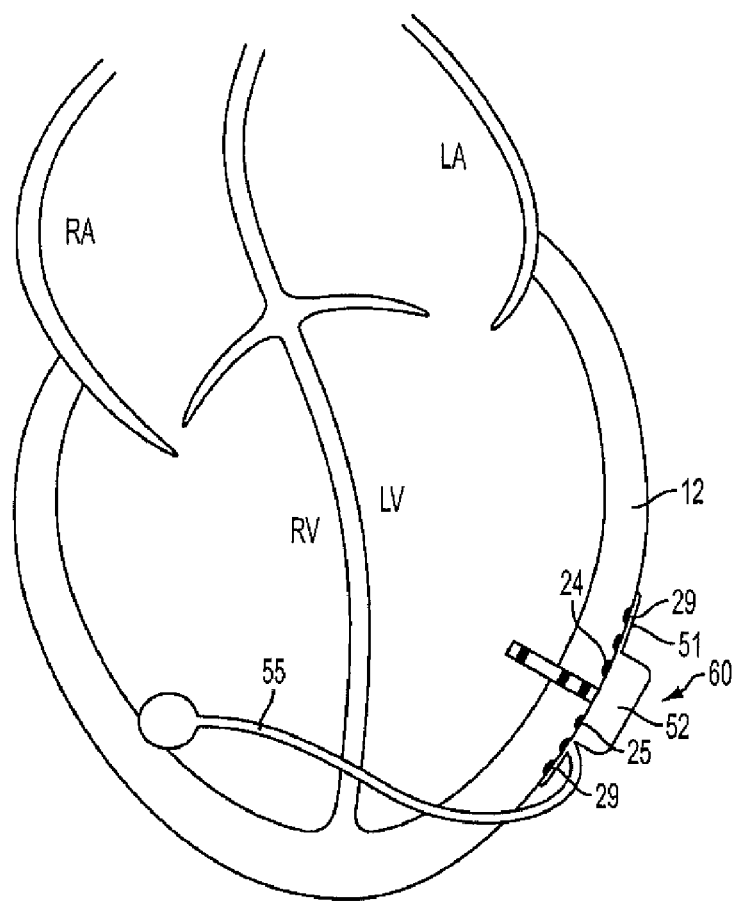
FIG. 3A is a schematic presentation of the second embodiment of the invention.
Figure 3B:
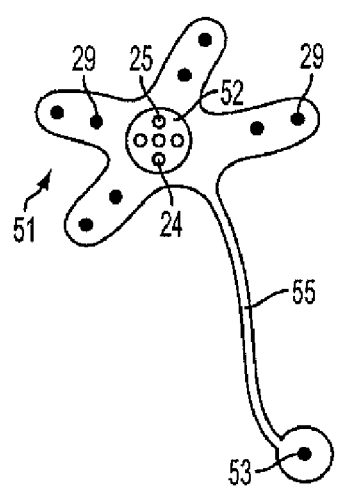
FIG. 3B is a schematic presentation of the second embodiment of the invention.
Figure 4:
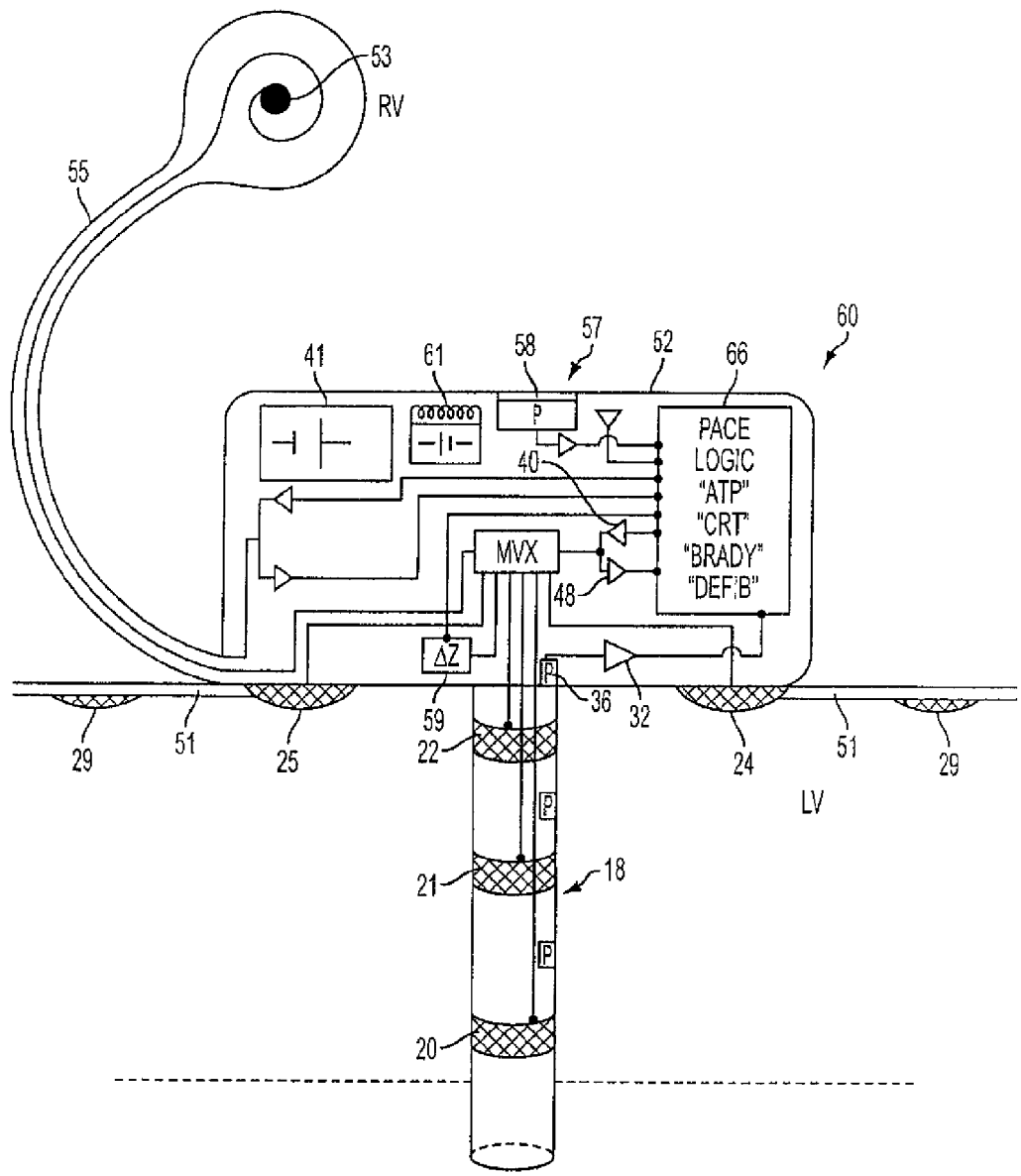
FIG. 4 is a schematic presentation of the second embodiment of the invention.

FIGS. 3A-3B and 4 show an implantable device 60 attached to the epicardial wall of the left ventricle 12, and a connected lead 55 that extends form the device 60 so that an electrode at its distal end is positioned adjacent to right ventricle. In the FIG. 3A embodiment, a fabric patch may be used to form an electrode array structure 51 to support multiple electrode sites that radiate from device housing 52 in a starfish like pattern best seen in FIG. 3B.

As with the fabric fixation patch 14 used in the FIG. 1 embodiment, the fabric patch electrode array structure 51 may be attached to a surface of the device housing 52 that is positioned against the LV wall 12 to permit and promote tissue growth to anchor the device 60 to the wall 12. The epicardial surface electrodes on the array structure 51, typified by electrode 29, alone or in combination with electrodes 25 and 27, may be used for pacing, ATP, vector cardio graphic EGM signal analysis and impedance measurement, in different implementations of the invention. In the present example structure, the electrode array structure 51 has eight electrodes, with two electrodes positioned in each of two arms of the starfish like pattern.

A transmural member 18 extends from the device housing 52 though the LV wall 12. In this embodiment the transmural member 18 carries three electrodes and a pressure transducer to sense pressure in the left ventricle 20. An electrode located on or around the device housing 52 may be used as an LV defibrillation electrode. A companion right ventricular lead 55 is coupled to the device 60. In this example, the ventricular lead 55 includes a patch-type defibrillation electrode that is shown in the FIG. 3A as having been sutured or otherwise secured to an external surface of the RV. Sense amplifier and pulse output circuitry is provided in the device housing 52 to sense (via "far field" techniques, for example) LA electrical activity and to sense and pace the RV and LV, as well as to provide defibrillation pulses (for example, between one or more of the electrodes associated with the device 60, on one hand, and the patch electrode of lead 55, on the other hand.

In this configuration, the relatively large surface area of electrode in the vicinity of the LV wall and the RV patch electrode placement enables optimal energy delivery without compromising the myocardial tissue. In addition, the positioning of the electrodes used to deliver defibrillation pulses provide for optimal distribution of a defibrillating electrical field that confines most of the defibrillation shock energy to the ventricular tissues. It is expected that the optimal energy distribution will permit more effective treatment at lower energy levels. As such, reduced energy requirements may be more easily met, given a particular housing volume, with LV epicardial placement of the device 60 and RV placement of the lead 55. In addition, confinement of the electrical field to myocardium may avoid painful stimulation of skeletal muscle during defibrillation shock.

For ATP pacing an array of electrodes is available on electrode array 51 (eight such electrodes 29 in the FIG. 3B embodiment) and epicardial electrodes 25 and 27 to provide ATP pacing distributed over a wider area to facilitate more effective arrest of a circus rhythm. Such electrodes 29 may have a size, for example, of two millimeters in diameter.

Described in connection with not only FIG. 3A but also the more detailed FIG. 4 are three useful features: 1) an array of electrodes on the bottom of the button (in other words, on a surface of the housing 52 that contacts the epicardial surface, as with electrodes 25 and 27 in FIG. 4), 2) ATP electrodes that are capable of being distributed over a wider area of the epicardium with a network of unfolding electrodes formed on flexible surfaces, and 3) biventricular synchronized ATP that allows maximum capture of ventricular tissue.

FIG. 4 shows the device 60 in isolation while components in the housing 52 are illustrated schematically. The transmural member 18 is coupled to a sensor (labeled "P") that transduces the LV pressure to a signal conditioned by interface circuit 32. The transduced signal provides pressure data to the logic circuit 66. The logic circuit 66 carries out many functions and may issue a left ventricular VP signal to activate stimulation circuit 40. An LV stimulus when required may be delivered between, for example, electrode 58 on the transmural member 18, and a nearby electrode on the transmural member 18. The epicardial electrodes 25 and 27 on the surface of the housing 52 that contacts the epicardial surface of the LV have a relatively large distributed area (not each individually, but all electrodes combined, which in this example is two) for more effective ATP. In another embodiment the ATP electrodes 29 are distributed over a wider area with a network of unfolding electrodes on an electrode array structure connected to the device housing. This array configuration for ATP will also be useful in the pacing embodiment presented with respect to FIG. 1 and FIG. 2. In addition, in FIG. 1 the most distal ring electrode 20 is depicted in the blood pool, while in FIG. 4 the most distal electrode is shown in the myocardial wall in an endocardial position. Both are useful locations for sensing and pacing and other functions.

Other bipolar or unipolar electrode configurations are possible with the set of optional electrodes seen in FIG. 4. The LV EGM is also available through sense amplifier 48. All of the circuitry is powered by a primary cell 41 or rechargeable battery 61.

The ability to stimulate both the RV and LV permits the logic 66 to carry out and order cardiac resynchronization therapy (CRT), bi-ventricular ATP, and defibrillation protocols, in addition to the traditional dual chamber pacing modalities that are familiar to those skilled in this art and need not be explained in detail.

The LV pressure permits the measurement of actual A to V activation times, as well as the selection of a pacing AV delay to maximize cardiac output for a beat. The LV pressure and EGM data can be used to discriminate arrhythmia and direct ATP therapy or defibrillation shock.

Telemetry circuitry associated with logic 34 (or 66 in the FIG. 4 embodiment) can set pacing parameters for the devices 10 or 60 in any known ventricular synchronized pacing mode or protocol. The AV delay of the pacing mode can be adjusted manually or automatically in ambulatory setting to a hemodynamically optimal value. The parameters for ATP can be set via telemetry and the RV to LV conduction time can be measured and set to a more optimum value with the available LV pressure data.

The defibrillation embodiment has several electrodes that improve EGM sensing and can be used to monitor tissue ischemia via impedance sensor 59. These electrodes permit improved sensing and discrimination of electrical events as well as therapy administration. Consequently better decisions to pace or defibrillate can be made in real time.

The device 60, as shown in FIG. 4, includes a companion intrathoracic pressure sensor 57 located within the device housing 52. In particular, the pressure sensor 57 is positioned adjacent to a wall of the device housing 52, and may include a diaphragm structure 58 that is reactive to pressure forces outside of the device housing 52. Pressure indications produced by the pressure 57 may indicate an ambient barometric pressure, and may be used to correct pressure readings from within the ventricle (by pressure transducer 36, for example). In addition, the pressure indications produced by pressure sensor 57 may be used to detect a respiration rate of the patient, which information may be used to adjust pacing based on metabolic demand or provide rate-responsive pacing therapy.

Transducer Lead Embodiment

Figure 5:
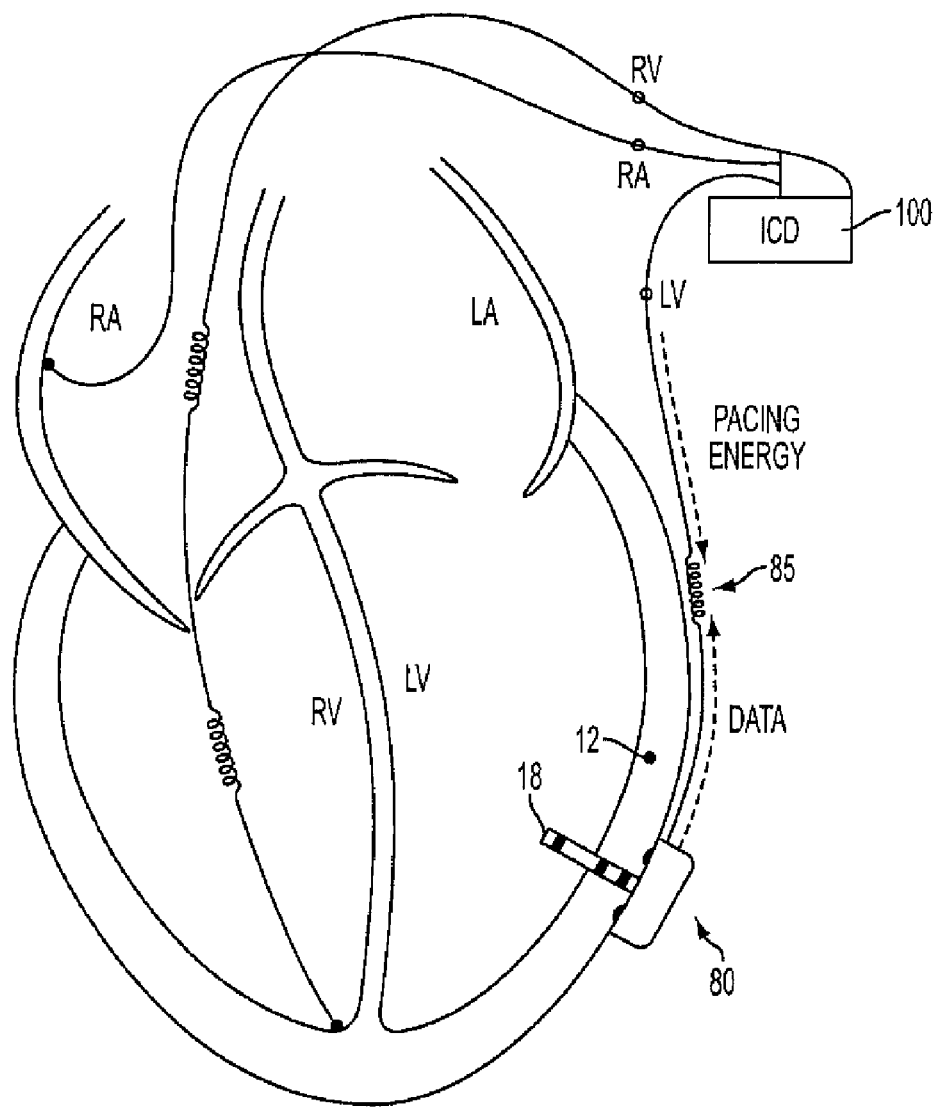
FIG. 5 is a schematic presentation of the third embodiment of the invention; and, FIG. 6 is a schematic presentation of the third embodiment of the invention.

FIG. 5 shows an implantable device 80 similar to those described previously implanted on the LV. The electrodes on the transmural member 18 are coupled to the remote ICD 100 or to a subcutaneous device that primarily supplies power via the lead body. In this configuration the ICD uses the device 80 as an alternative to a conventional LV lead.

It is preferred in this embodiment to incorporate a pressure transducer and several electrodes on the device 80.

In general the pressure data will permit the device to cooperate with the ICD to distinguish rhythms based in part on the hemodynamic characteristics. Hemodynamically stable slow and fast VTs may be treated with ATP. More accurately detected VF may be interrupted with a high voltage shock delivered through the conventional RV leads associated with the ICD. The button device 80 can serve as a pole for optimal energy field propagation. In another embodiment the lead connecting the device 80 and an ICD can have a large surface area coil electrode 85 for optimal energy field propagation during defibrillation shock. The ATP treatment is expected to be more effective because of the larger total surface area of epicardial electrodes and synchronous bi-ventricular ATP.

Figure 6:
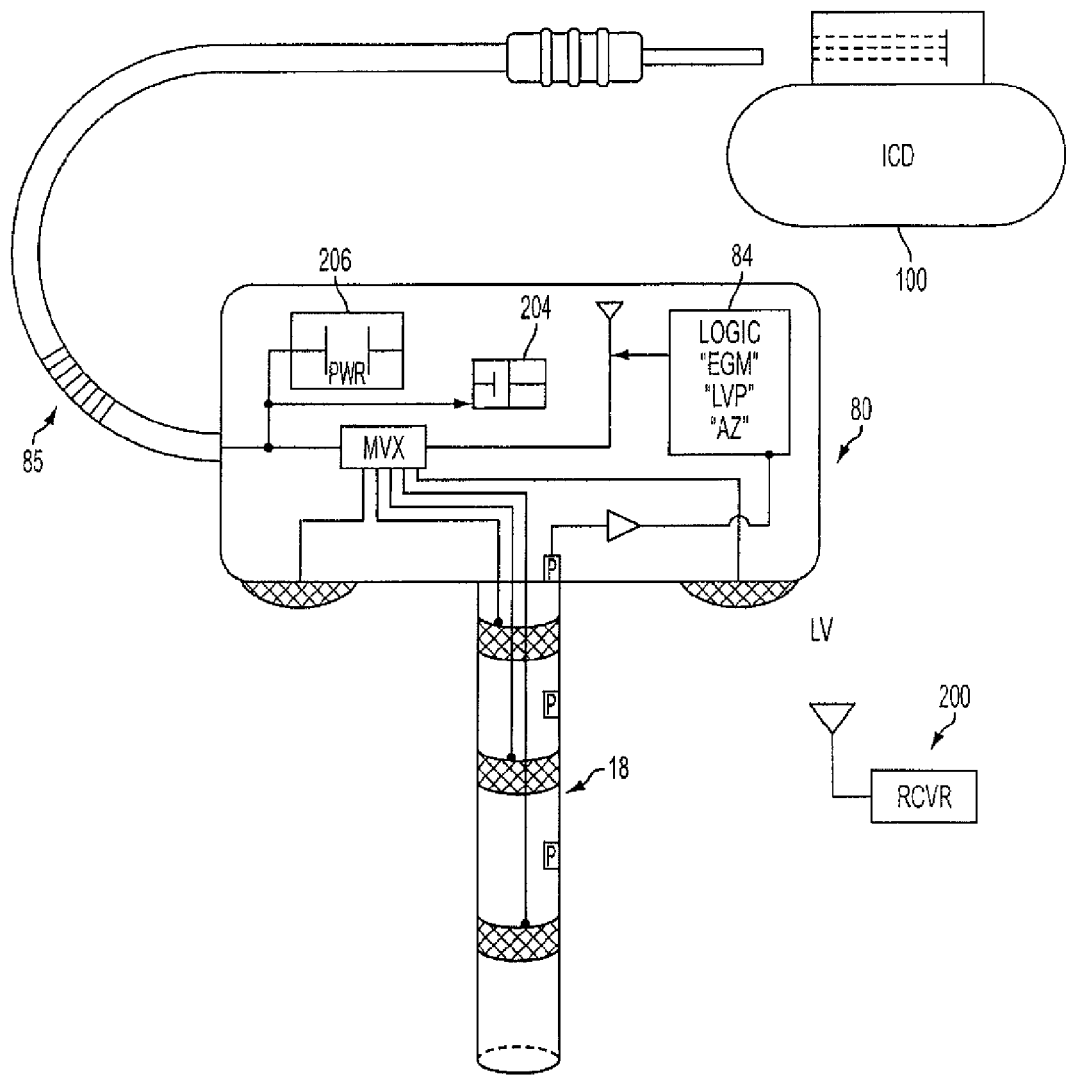

FIG. 6 depicts the internal architecture of the device 80 and elements of a system including a remote telemetry receiver 200. The device 80 may be relatively "dumb" if the companion device provides a high degree of functionality to provide ATP, CRT and bradycardia pacing. In this instance the logic 84 may simply format and transmit LV pressure data to the ICD 100 to facilitate the fibrillation detection with the additional hemodynamic factors. Truncation of therapy and initiation of bradycardia support can be based on hemodynamic considerations as well. If the ICD is "dumb" then additional functions may be implemented in the device 80. For example the decision to provide or withhold high voltage shocks could be made in the device 80 based on pressure data and EGM.

In either embodiment the pressure data may be made available remotely for patient management to the remote receiver 200. In addition if the LV pressure data indicates that the cardioversion or defibrillation therapies are not successful then an alert or warning signal may be sent to the remote receiver for use by the patient the doctor, emergency response team or all of them.

In this embodiment the ICD can power the device 80 by supplying pulses to the device to recharge a battery 204 or capacitor 206 to power the logic within the device.

What is claimed is:

1. An implantable device for managing heart rhythm, comprising:
   a device housing for implantation on the epicardial surface of the left ventricular wall;
   a transmural member extending from said device housing and adapted for implantation across the left ventricular wall;
   one or more electrodes located on said transmural member, said electrodes to perform one or more of the following functions: a) sensing or b) pacing;
   a logic circuit located within said device housing for pacing the left ventricle in response to electrical activity of the heart.

2. The device of claim 1, further comprising:
   a pressure sensor proximate said device housing for measuring left ventricular pressure;

and wherein said logic circuit located within said device housing paces the left ventricle in response to electrical activity of the heart and measured left ventricular pressure.

3. The device of claim 1, wherein an array of electrodes is attached to the device housing and located on the epicardial surface of the left ventricular wall.

4. The device of claim 1, wherein said logic circuit carries out bradycardia and antitachy cardiac pacing modalities.

5. The device of claim 4, wherein for bradycardia modalities that call for an AV delay interval, said AV delay is determined at least in part from said measured left ventricular pressure and sensed electrical activity of the heart.

6. The device of claim 1, further including a reference pressure transducer associated with said device housing for monitoring intrathoracic pressure.

7. The device of claim 6, wherein said reference pressure transducer is used to detect respiration.

8. The device of claim 7, wherein the device is adapted to adjust pacing based on metabolic demand determined from detected respiration.

9. The device of claim 6, wherein said reference pressure transducer is used compensate the LV pressure measurements.

10. The device of claim 1, wherein the transmural member comprises multiple different electrodes formed on a surface of the transmural member.

11. The device of claim 1, wherein the transmural member comprises both electrically conductive portions and non-electrically conductive portions.

12. An implantable device for managing heart rhythm, comprising:
- a device housing for implantation on the epicardial surface of the left ventricular wall;
- a transmural member extending from said device housing said transmural member adapted for implantation in the left ventricular wall;
- one or more electrodes located on said transmural member, said electrodes to perform one or more of the following functions: a) sensing or b) pacing;
- a right ventricular lead connectable to said device housing; and
- a logic circuit located within said device housing for pacing the left ventricle and/or the right ventricle in response to electrical activity of the heart.

13. The device of claim 12, further comprising:
- a pressure sensor proximate said device housing for measuring left ventricular pressure;
- and wherein said logic circuit located within said device housing paces the left ventricle and the right ventricle in response to electrical activity of the heart and the measured left ventricular pressure.

14. The device of claim 12, wherein said logic circuit carries out bradycardia and antitachycardia pacing modalities.

15. The device of claim 14, wherein the AV delay and/or the RV to LV pacing intervals are determined by said measured left ventricular pressure and electrogram.

16. A system including an implantable epicardial device for managing a heart rhythm in combination with a subcutaneous device of the type having a lead connector, said implantable epicardial device comprising:
- a device housing for implantation on the epicardial surface of the left ventricular wall;
- a coupling lead connecting said subcutaneous device with said device housing, for coupling said subcutaneous device and said epicardial device together;
- a transmural member extending from said epicardial device housing said transmural member adapted for implantation in the left ventricular wall;
- one or more electrodes located on said transmural member, said electrodes to perform one or more of the following functions: a) sensing or b) pacing;
- a pressure transducer proximate said epicardial device housing for measuring left ventricular pressure and providing pressure data to said subcutaneous device;
- a logic circuit for measuring LV pressure data and transmitting the data to said subcutaneous device to invoke a defibrillation therapy based at least in part on sensed ventricular pressures.

17. The system of claim 16, wherein said coupling lead transfers power to said epicardial device housing.

18. The system of claim 16, wherein said coupling lead transfers pacing energy to said epicardial device housing for delivery to said one or more electrodes.

19. The system of claim 16, wherein the failure to convert an arrhythmia results in the telemetry of a warning signal to a remote receiver.

20. The system of claim 16, wherein the implantable device is connected to a pacemaker.

21. The system of claim 16, wherein the implantable device is connected to an ICD.

22. An implantable device for managing heart rhythm, comprising:
- a device housing for implantation on the epicardial surface of the left ventricular wall;
- a transmural member extending from said device housing and adapted for implantation across the left ventricular wall;
- one or more electrodes located on said transmural member, said electrodes adapted to sense electrical activity of the left ventricular wall and provide pacing stimuli to the left ventricular wall; and
- a logic circuit within said device housing, the logic circuit adapted to provide the pacing stimuli to the one or more electrodes to pace the left ventricle in response to electrical activity of the heart.

* * * * *